(12) United States Patent
Firer et al.

(10) Patent No.: US 7,772,179 B2
(45) Date of Patent: Aug. 10, 2010

(54) PHOTODYNAMIC THERAPY USING CHEMILUMINESCENCE AND A LIGAND-PHOTOSENSITISER CONJUGATE

(75) Inventors: Michael A. Firer, Ginot Shomron (IL); Raisa Laptev, Ariel (IL)

(73) Assignee: Ariel-University Research and Development Company Ltd., Ariel (IL)

( * ) Notice: Subject to any disclaimer, the term of this patent is extended or adjusted under 35 U.S.C. 154(b) by 258 days.

(21) Appl. No.: 11/918,905

(22) PCT Filed: Apr. 20, 2006

(86) PCT No.: PCT/IL2006/000487

§ 371 (c)(1),
(2), (4) Date: Oct. 19, 2007

(87) PCT Pub. No.: WO2006/111971

PCT Pub. Date: Oct. 26, 2006

(65) Prior Publication Data

US 2009/0054306 A1 Feb. 26, 2009

(30) Foreign Application Priority Data

Apr. 21, 2005 (IL) .................... 168184

(51) Int. Cl.
*A61K 38/02* (2006.01)
*A61K 38/40* (2006.01)
*A61K 41/00* (2006.01)
*C07K 1/113* (2006.01)
*C07K 14/79* (2006.01)

(52) U.S. Cl. ............. 514/2; 514/8; 514/21; 530/345; 530/394; 530/402; 530/409

(58) Field of Classification Search ............. None
See application file for complete search history.

(56) References Cited

U.S. PATENT DOCUMENTS

| 4,181,650 | A | * | 1/1980 | Maier, Jr. ............ 530/303 |
| 4,870,002 | A | * | 9/1989 | Kiel ............ 435/2 |
| 5,257,970 | A | | 11/1993 | Dougherty |
| 5,952,311 | A | | 9/1999 | Kraus et al. |
| 6,554,853 | B2 | | 4/2003 | Chen |
| 7,001,991 | B2 | | 2/2006 | Faulk |

FOREIGN PATENT DOCUMENTS

EP   515194 A2 * 11/1992

OTHER PUBLICATIONS

Carpenter et al. "Chemiluminescent Activation of the Antiviral Activity of Hypericin: A Molecular Flashlight", Proc. Natl. Acad. Sci. USA, 91: 12273-12277, 1994.

(Continued)

*Primary Examiner*—Jeffrey E Russel

(57) ABSTRACT

A method for destroying harmful cells is provided, applicable in treating proliferative diseases. The cells are destroyed by a combined treatment with a chemiluminescent agent and with a ligand-photosensitizer conjugate. The chemiluminescent agent emits light on reacting with oxygen species present in situ, the conjugate binds to the cell through its ligand and is activated by the emitted light, thereby destroying the cell. The method is demonstrated on a conjugate of transferrin-hematoporphyrin, which destroys cancerous cells in the presence of luminol.

26 Claims, 7 Drawing Sheets

OTHER PUBLICATIONS

Cavanaugh "Synthesis of Chlorin E6-Transferrin and Demonstration of Its Light-Dependent in Vitro Breast Cancer Cell Killing Ability", Breast Cancer Research and Treatment, 72(2): 117-130, 2002.

Laptev et al. "Intracellular Chemiluminescence Activates Targeted Photodynamic Destruction of Leukaemic Cells", British Journal of Cancer, 95(2): 189-196, 2006.

Phillip et al. "Chemiluminescence and Hematoporphyrin Derivative: A Novel Therapy for Mammary Adenocarcinomas in Mice", Oncology, 46(4): 266-272, 1989.

Sharman et al. "Targeted Photodynamic Therapy Via Receptor Mediated Delivery Systems", Advanced Drug Delivery Reviews, 56(1): 53-76, 2004.

Theodossiou et al. "Firefly Luciferin-Activated Rose Bengal: In Vitro Photodynamic Therapy by Intracellular Chemiluminescence in Transgenic NIH 3T3 Cells", Cancer Research, 63(8): 1818-1821, 2003.

Vrouenraets et al. "Basic Principles, Applications in Oncology and Improved Selectivity of Photodynamic Therapy", Anticancer Research, 23(1B): 505-522, 2003.

International Preliminary Report on Patentability Dated Nov. 1, 2007 From the International Bureau of WIPO Re.: Application No. PCT/IL2006/000487.

International Search Report Dated May 23, 2007 From the International Searching Authority Re.: Application No. PCT/IL2006/000487.

Office Action Dated Sep. 4, 2008 From the Israeli Patent. Office Re.: Application No. 168184.

Response Dated Jul. 9, 2008 to Communication Pursuant to Article 94(3) EPC of Mar. 6, 2008 From the European Patent Office Re.: Application No. 06728287.1.

Written Opinion Dated May 23, 2007 From the International Searching Authority Re.: Application No. PCT/IL2006/000487.

Office Action Dated Jun. 10, 2009 From the Israeli Patent Office Re.: Application No. 168184 and Its Translation Into English.

Response Dated Dec. 10, 2009 to Office Action of Jun. 10, 2009 From the Israel Patent Office Re.: Application No. 168184.

* cited by examiner

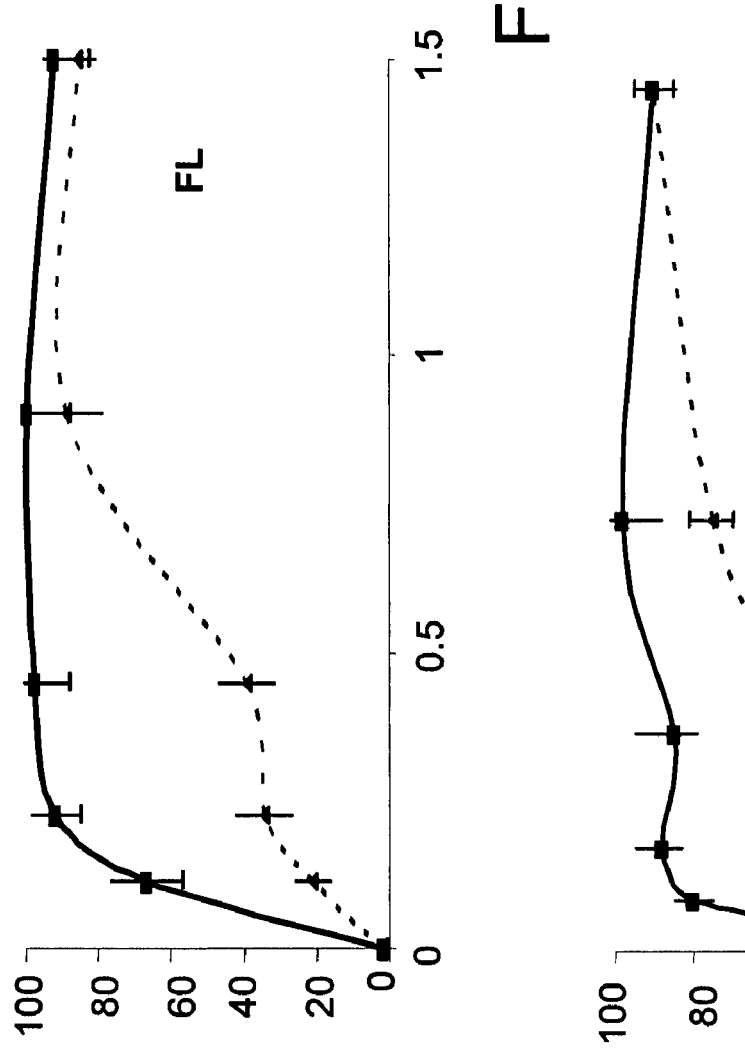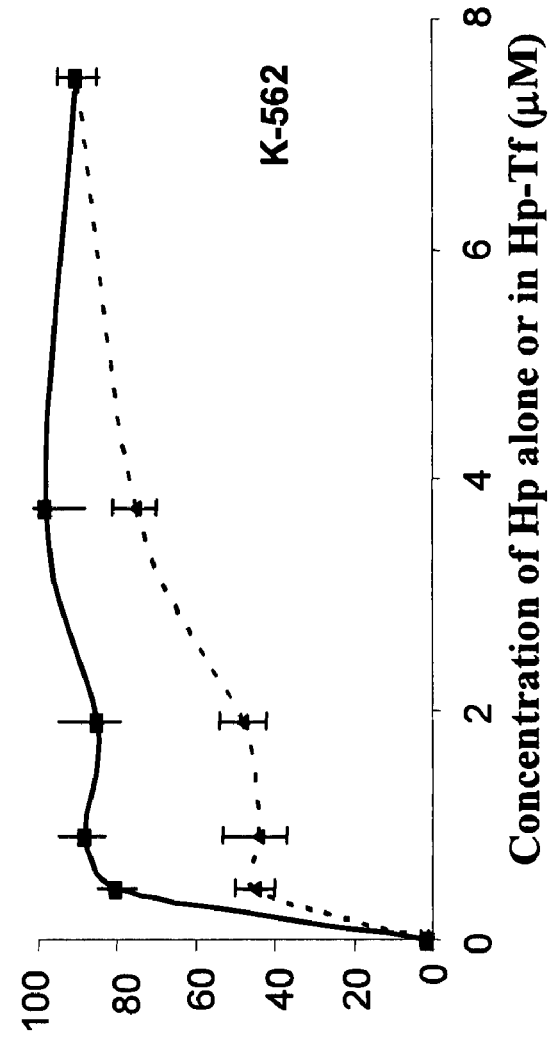

Table 1

| Parameter | Cell Type | | |
|---|---|---|---|
| | FL | K-562 | U-7 |
| Concentration at $LD_{50}$ (μM) | | | |
| Hp | 0.55 | 1.9 | NR |
| Tf-Hp | 0.08 | 0.3 | 0.5 |
| Ratio# | 6.88 | 6.33 | ---- |
| Concentration at $LD_{90}$ (μM) | | | |
| Hp | NR | 7.5 | NR |
| Tf-Hp | 0.18 | 1.0 | >3.5 |
| Ratio# | ------ | 7.5 | ----- |
| Concentration at LDMAX (μM) | | | |
| Hp | 0.89 | 7.5 | 3.0 |
| Tf-Hp | 0.45 | 3.75 | 3.0 |
| Ratio# | 1.98 | 2.0 | 1.0 |
| % Cell Cytotoxicity at LDMAX | | | |
| Hp | 84 | 90 | 40 |
| Tf-Hp | 100 | 100 | 85 |
| Ratio# | 0.84 | 0.90 | 0.47 |

\#: Ratio of Hp/Tf-Hp    NR: Not reached

Fig. 3

PHOTODYNAMIC THERAPY USING CHEMILUMINESCENCE AND A LIGAND-PHOTOSENSITISER CONJUGATE

RELATED APPLICATIONS

This Application is a National Phase of PCT Patent Application No. PCT/IL2006/000487 having International Filing Date of Apr. 20, 2006, which claims the benefit of Israel Patent Application No. 168184 filed on Apr. 21, 2005. The contents of the above Applications are all incorporated herein by reference.

FIELD OF THE INVENTION

The present invention relates to a method for destroying selected target cells by a combined treatment using a ligand-toxin conjugate and a chemiluminescent agent, wherein the conjugate comprises a photosensitizer, such as hematoporphyrin.

BACKGROUND OF THE INVENTION

The low target specificity of chemotherapeutic agents has stimulated development of targeted drug delivery strategies such as ligand-toxin conjugates (LTCs), involving the coupling of an effecter molecule to a transport ligand that is directed to a target cell-specific receptor [see, e.g., Mrsny R. J.: Expert Opinion on Biological Therapy 4 (2004) 65-73]. Ligands such as small molecules have advantages over larger molecules like antibodies. The instant inventors recently reported on the use of small molecule-containing LTCs for the targeted destruction of plasma cells [Firer M. A. et al.: Leukemia and Lymphoma 44 (2003) 681-9], suggesting that this approach may be applicable for multiple myeloma therapy. The LTC strategy represents one aspect of the present invention. Another aspect involves Photodynamic Therapy (PDT), a two-stage procedure based on two non-toxic components that combine to induce membrane alterations leading to cytolysis. The first component is a photosensitizer (Ps) molecule, usually a porphyrin derivative, that transfers energy to molecular oxygen when light-activated, producing reactive oxygen species that cause direct damage to cellular components, particularly membrane phospholipids. PDT is believed to mediate tumor cell destruction by at least two additional mechanisms: destruction of tumor vascular cells, and the induction of both inflammatory and immune anti-tumor reactions. The history, mechanism of action and biomedical applications of PDT have been the subject of several reviews [see, e.g., Sharman W. M. et al.: Adv. Drug Delivery Rev. 56 (2004) 53-76]. Two major problems limit the wider application of PDT as a treatment modality. First, since photosensitizers tend to accumulate in tumor tissue, toxic side-effects may preclude their clinical use. To overcome this problem, Ps was covalently linked to carrier molecules so as to localize the PDT effect to a target cell. [e.g., Brown S. B. et al.: (2004). Lancet Oncol. 5 (2004) 497-508]. One attractive carrier protein-receptor system for this purpose utilizes the high affinity interaction between the iron-transporter transferrin (Tf) and its cell-surface receptor (TfR, CD71). As all dividing cells require a continuous supply of iron for metabolism, it is not surprising that TfR is over-expressed on a variety of malignant cells [Ponka P. et al.: Sem. Hematol. 35 (1998) 35-54], so the Tf-TfR system has been used in several formats to target Ps compounds to different types of malignant cells [Hamblin M. R. et al.: J. Photochem. Photobiol. 26 (1994) 45-56; Rittenhouse-Diakun K. et al.: Photochem. Photobiol. 61 (1995) 523-8; Cavanaugh P. G. Breast Cancer Res. Treat. 72 (2002) 117-30; Gijsens A. et al.: Int. J. Cancer. 101 (2002) 78-85; Li H. et al.: Med. Res. Rev. 22 (2002) 225-50]. The second major problem regarding PDT is the limited tissue penetration of the external light. Despite advances in the development of external light devices for phototherapy, and the successful clinical use of PDT for peripheral cancers and in dermatology, the treatment of internal body tissues remains limited to invasive procedures, such as the use of catheters. There have been attempts to develop molecular approaches to Ps activation. Carpenter [Carpenter S. et al.: Proc. Natl. Acad Sci. USA 91 (1994) 12273-7] employed intracellular bioluminescent activation of hypericin and the subsequent destruction of equine dermal cells, while Phillip [Phillip M. J. et al.: Oncology 46 (1989) 266-72] used a hematoporphyrin derivative (Photofrin II) and a multi-component solution to induce intracellular CL in mammary adenocarcinomas. However, the existing systems do not provide sufficient specificity and efficiency of PDT. It is therefore an object of this invention to provide a bioconjugate with significantly improved parameters. Luminol (5-amino-2-3-dihydro-1,4-phtalazinedione) has been successfully used in a variety of CL-based assays systems [Kricka J. L.: Ann. Clin. Biochem. 39 (2002) 114-29; Templin M. F. et al.: Drug. Discov. Today 7 (2002) 815-22]. The mechanism of the CL reaction of luminol has been known for some time, and while some physico-chemical aspects of luminol activation in macrophages have been examined [Nemeth A. et al.: Biochem. Biophys. Res. Comm. 255 (1999) 360-6], the luminol-PDT connection has never been exploited to induce PDT cytotoxicity in tumor cells. It is therefore another object of the present invention to provide a PDT comprising a LTC and a chemiluminescent agent.

Other objects and advantages of present invention will appear as description proceeds.

SUMMARY OF THE INVENTION

The invention provides a method for destroying selected target cells comprising steps of i) exposing said cells to a chemiluminescent activating agent (CA), and ii) binding to said cells a ligand-toxin conjugate (LTC) comprising a photosensitizer (Ps). Said CA produces chemiluminescent light, which activates said Ps, which transfers energy to molecular oxygen and produces reactive oxygen species, causing damages to said target cells. Said CA produces said light by reacting with an oxygen species present in situ. In the method of the invention, said steps i) and ii) may be performed in any order or simultaneously. In addition, the CA and LTC may be coupled by various means. Said LTC comprises a small molecule, peptide or protein, or other factor having affinity to a component on the surface of the targeted cell, such as transferrin, which is intended to bind to a specific cell receptor such as transferrin receptor on said target cells. Said LTC preferably comprises hematoporphyrin as a Ps. In a preferred embodiment of the invention, LTC in a method for destroying target cells comprises transferrin and hematoporphyrin. The cells to be destroyed are preferably associated with a proliferative disease. Said cells may be a part of blood, skin, deep body tissues, or alternatively a cell culture. The invention provides a method for destroying cancerous cells.

The invention further relates to a method of treating in a subject a disorder associated with undesired cell proliferation or activity, comprising administering to said subject two components: a LTC comprising a Ps, and a CA. Said administering LTC and said administering CA may be performed in any order or simultaneously. Said LTC and CA may also be coupled together. Said LTC comprises preferably transferrin. Said Ps comprises preferably hematoporphyrin. In a preferred embodiment of the invention, transferrin and hematoporphyrin are conjugated in said LTC. Said disorder may be a cancerous disease or hyperplasia. Said disorder may include conditions in which the proliferation of cells contributes to the pathogenesis, including atherosclerosis, rheumatoid arthritis, psoriasis, idiopathic pulmonary fibrosis, scleroderma, cirrhosis, endometriosis, neovascularization, and tumors.

The invention also relates to combined use of a LTC comprising a Ps, and a CA for treating cancer, wherein said LTC preferably comprises transferrin and hematoporphyrin. Said CA may be coupled to said LTC, for example by a covalent link.

The invention provides a pharmaceutical composition comprising a ligand-toxin conjugate for use in treating a proliferative disease, wherein said ligand is transferrin, said toxin is a photosensitizer, and wherein said photosensitizer is activated in situ by a chemiluminescent agent. The invention also provides a pharmaceutical composition comprising a chemiluminescent agent for use in treating a proliferative disease, wherein said agent activates in situ a ligand-toxin conjugate.

The invention is also directed to a method for destroying harmful cells comprising steps of i) binding to said cells a ligand-toxin conjugate (LTC) comprising a photosensitizer (Ps); and ii) exposing said cells to a chemiluminescent agent (CA); thereby activating said photosensitizer, creating a reactive oxygen species, and inducing the cytolysis of said harmful cells.

BRIEF DESCRIPTION OF THE DRAWINGS

The above and other characteristics and advantages of the invention will be more readily apparent through the following examples, and with reference to the appended drawings, wherein:

FIG. 3. is Table 1, showing the comparison of cytotoxic efficiency of PDT induced by Tf-Hp or Hp for three cell lines;

FIG. 6. shows the effect of the two components, LTC and a chemiluminescent agent, on the cell cytotoxicity, in respect to the delay in their application, and to the order of their application.

DETAILED DESCRIPTION OF THE INVENTION

It has now been found that bioconjugates comprising hematoporphyrin (Hp) and carrier protein transferrin (Tf) significantly improve the specificity and efficiency of PDT for erythroleukemic cells, when applied with luminol. The observed synergistic toxic effect does not depend on the order in which the cells are contacted with a chemiluminescent agent and with a ligand-photosensitizer conjugate.

It is known that chemiluminescent agents (CL), such as luminol or isoluminol or lucigenin, emit light when being oxidized. Without wishing to be bound by theory, luminol appears, in a method according to the invention, to be induced to emit light after activation by in situ existing oxidizing factors which include molecular oxygen, or chemical groups and molecules capable of providing oxygen atoms or peroxides or other reactive oxygen species (ROS). Said oxidizing factors, such as oxygen or ROS, will induce the light emission, setting in motion a cascade of events including the formation of further ROS, activating the Ps component of the ligand-toxin conjugate, and ending with the cell destruction. This ROS and oxygen source, whether metabolically produced or provided by outside oxygen supply, prolongs the PDT cycle. A surprisingly low concentration of CL agent, not expected to be toxic by itself, is sufficient to kill the target cells. Furthermore, since the PDT components of the invention need not be present simultaneously, another problem of the prior art PDT is obviated, i.e., the requirement of the coordinated presence of several factors in the cell.

Figure 1:
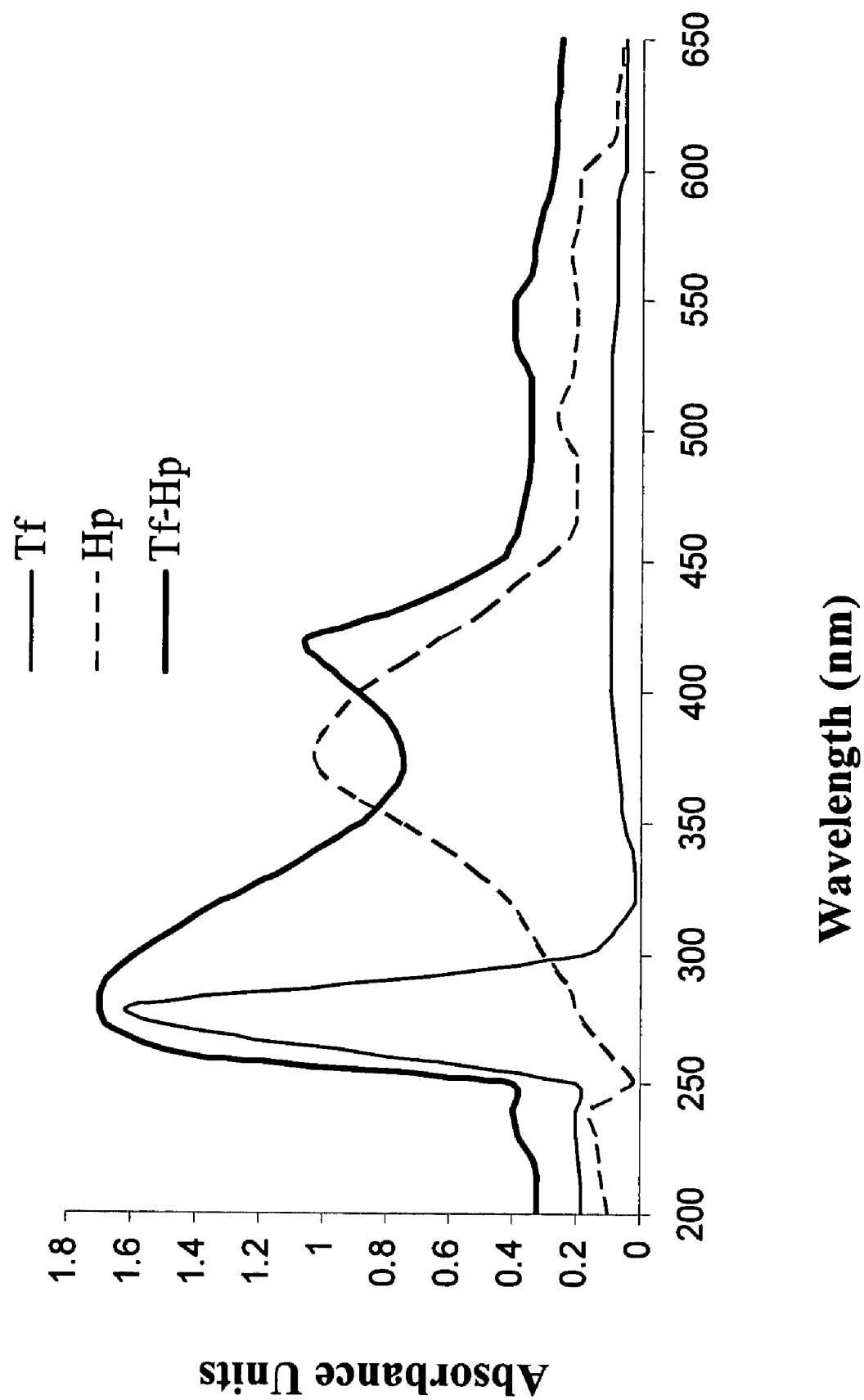
FIG. 1. shows UV-visible absorbance spectra of Tf, Hp, and Tf-Hp in PBS.

The preferred conjugate of the invention, Tf-Hp conjugate, was separated from Tf and Hp by HPLC and characterized by UV-Vis spectrophotometry (FIG. 1). The Tf spectrum reveals a typical maximum at $\lambda=280$ nm, whereas Hp absorption maximum is at $\lambda=375$ nm. The Hp-Tf conjugate has two absorption peaks at $\lambda=280$ nm and 412 nm and the spectrum is characterized by a red shift of the maximum and is not a simple superposition of the spectra of its components.

Figure 2C:
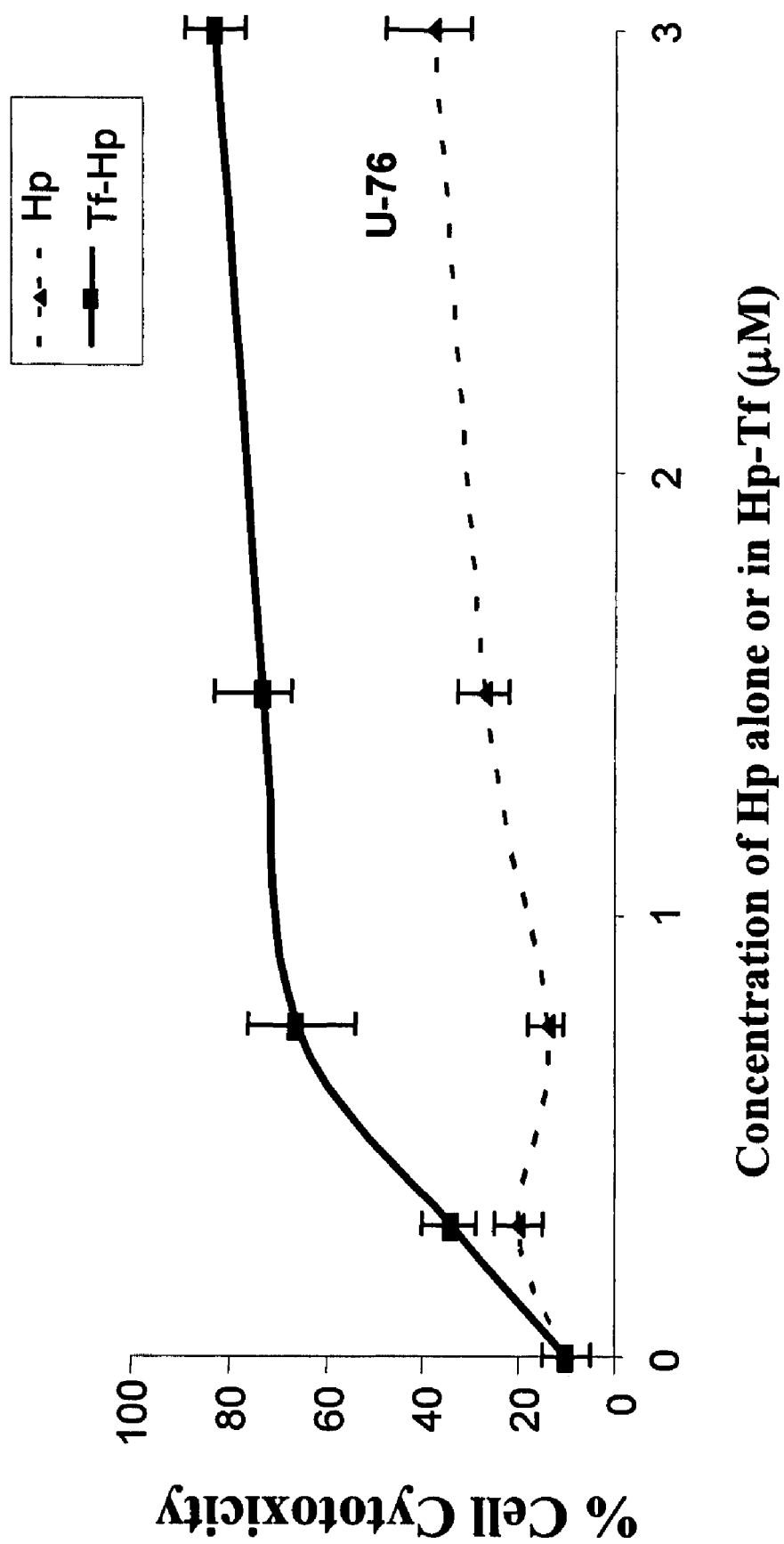
FIG. 2. demonstrates dose-dependent cytotoxicity of Hp and Tf-Hp for cells FL (A), K562 (B), and U-76. (C); 0.5-1×$10^5$ cells/ml were cultured for 2 hr in the dark in medium alone or containing Hp or Tf-Hp (0-3 µM), washed, exposed to ambient fluorescent light for 16 hrs at room temperature and then re-cultured in full medium for 24 hrs. Cell viability was assessed by trypan blue exclusion. The data represent the mean and standard deviation from at least 3 experiments.

FIG. 2 depicts the dose-response effect of Hp or Tf-Hp LTC treatment on the viability of FL, K562 and U-76 cells. Incubating the cells with various concentrations of Hp or Tf-Hp in the dark followed by overnight exposure to ambient fluorescent light showed that for all cell types, Tf-Hp was much more cytotoxic than Hp alone. FIG. 3 (Table 1) shows that the concentration of Tf-Hp required to achieve $LD_{50}$ was more than 6-fold lower than for Hp. Furthermore $LD_{100}$ values were only obtained with the Tf-Hp. U-76 hybridoma cells were relatively insensitive to PDT. The concentration of Tf-Hp required to reach $LD_{90}$ in these cells was >19.4 fold higher than for FL cells and >3.5 fold higher than for K-562 cells. This order of sensitivity was retained at the concentrations required for $LD_{MAX}$ (3.37 for FL and 0.8 for K562). Furthermore, 100% cytotoxicity was only obtained when the conjugate was used against the erythroleukemic cell lines. A similar pattern of sensitivity was also seen with free Hp treatment. While a similar (90%) $LD_{MAX}$ was reached for both erythroleukemic lines, FL cells were 16.6 more sensitive than K-562.

Figure 4:
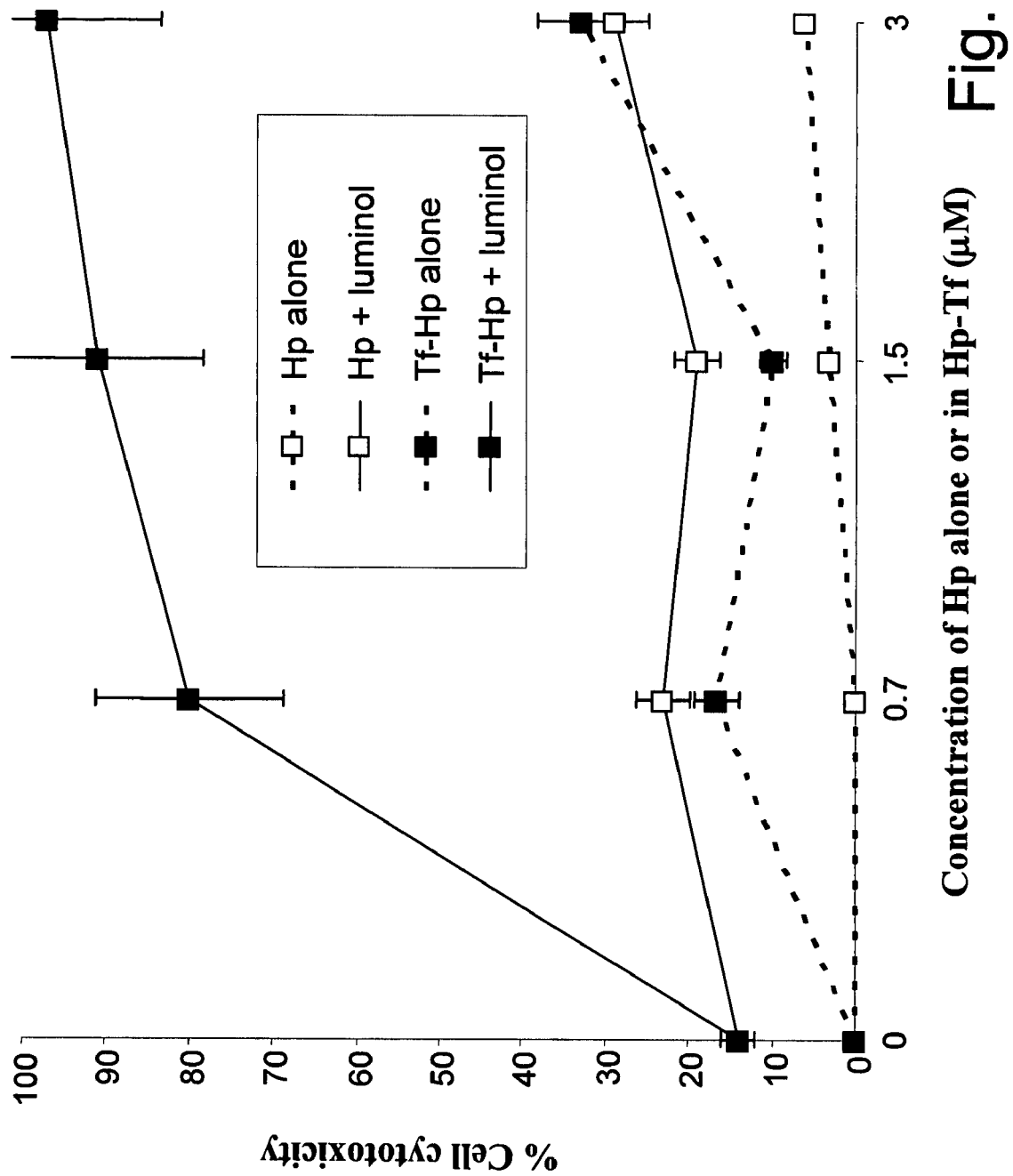
FIG. 4. shows the molecular intracellular activation of the PDT effect. FL cells were cultured in the dark for 48 hrs at 37° C. with hematoporphyrin (Hp) or hematoporphyrin-transferrin conjugate (Tf-Hp) (0-3 µM) together with 10 µM luminol. No other manipulation or external radiation of the cells was performed. At the end of the culture period, cell viability was determined by trypan blue exclusion.
Figure 5:
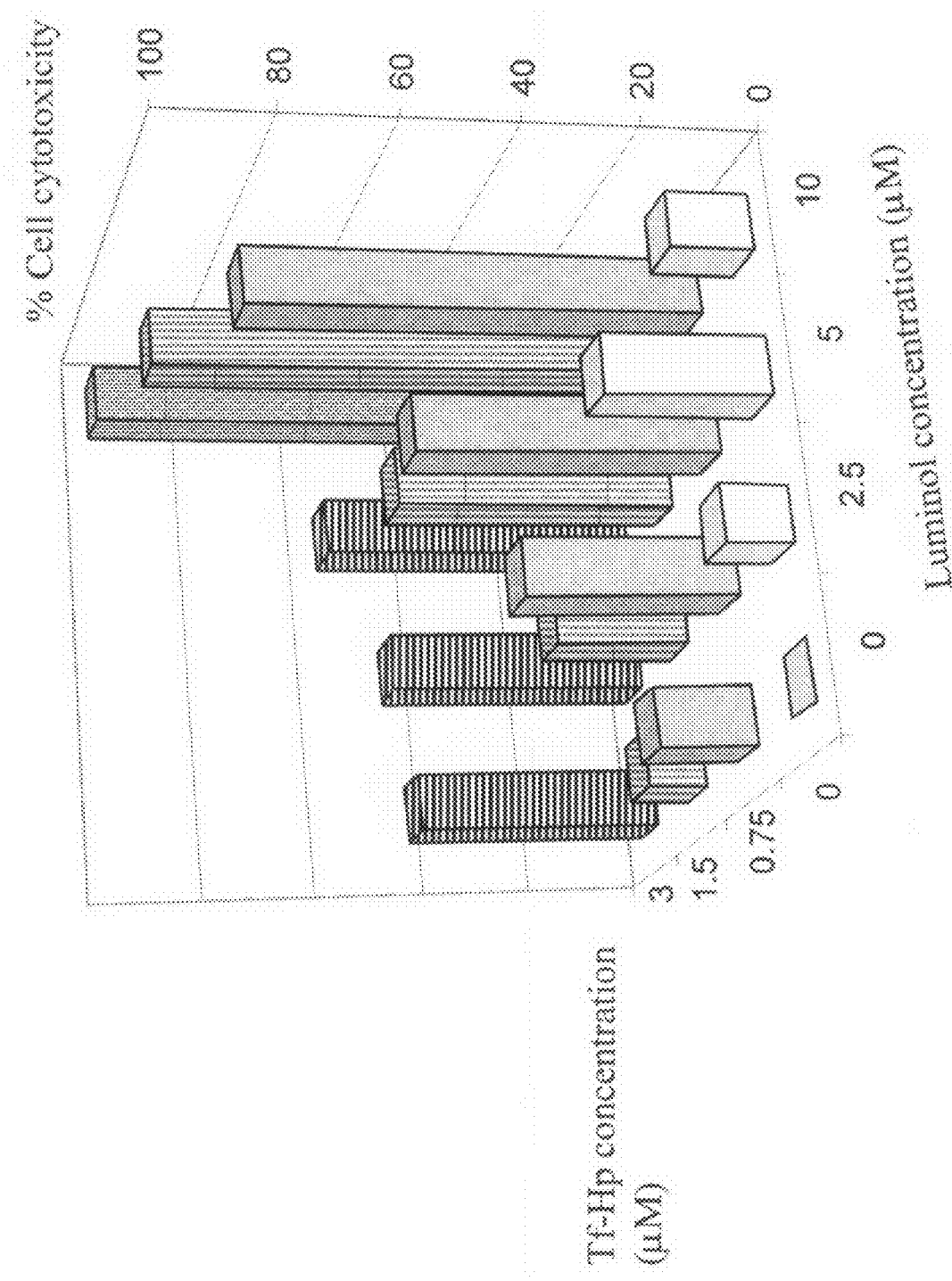
FIG. 5. is a graph showing the effect of the two components on the intracellular activation, in PDT. FL cells were cultured in the dark for 48 hrs at 37° C. with varying concentration combinations of hematoporphyrin-transferrin conjugate (Tf-Hp) (0-3 µM) and luminol. (0-10 µM). No other manipulation or external radiation of the cells was performed. At the end of the culture period, cell viability was determined by trypan blue exclusion.
Figure 6A:
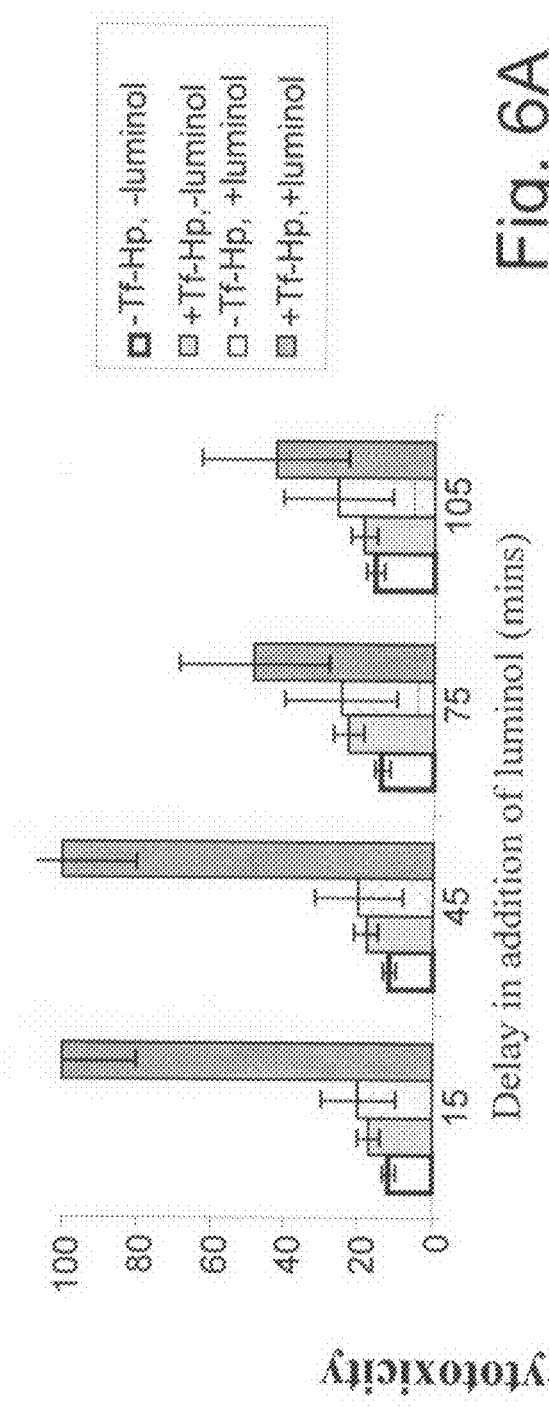
FIG. 6A shows the effect of delayed PDT activation by luminol on cytotoxicity of Tf-Hp treated FL cells. The cells were cultured for 2 hrs in the dark at 37° C. with Tf-Hp (3 µM) and washed. After various delay times (0, 30, 60 or 90 min), luminol (5 µM) was added and the cells were further cultured for 16 hrs in the dark. The figure shows the % of induced cytotoxicity. The 0 delay point includes time for washing of the cells and returning them to the culture (approximately 15 min).
Figure 6B:
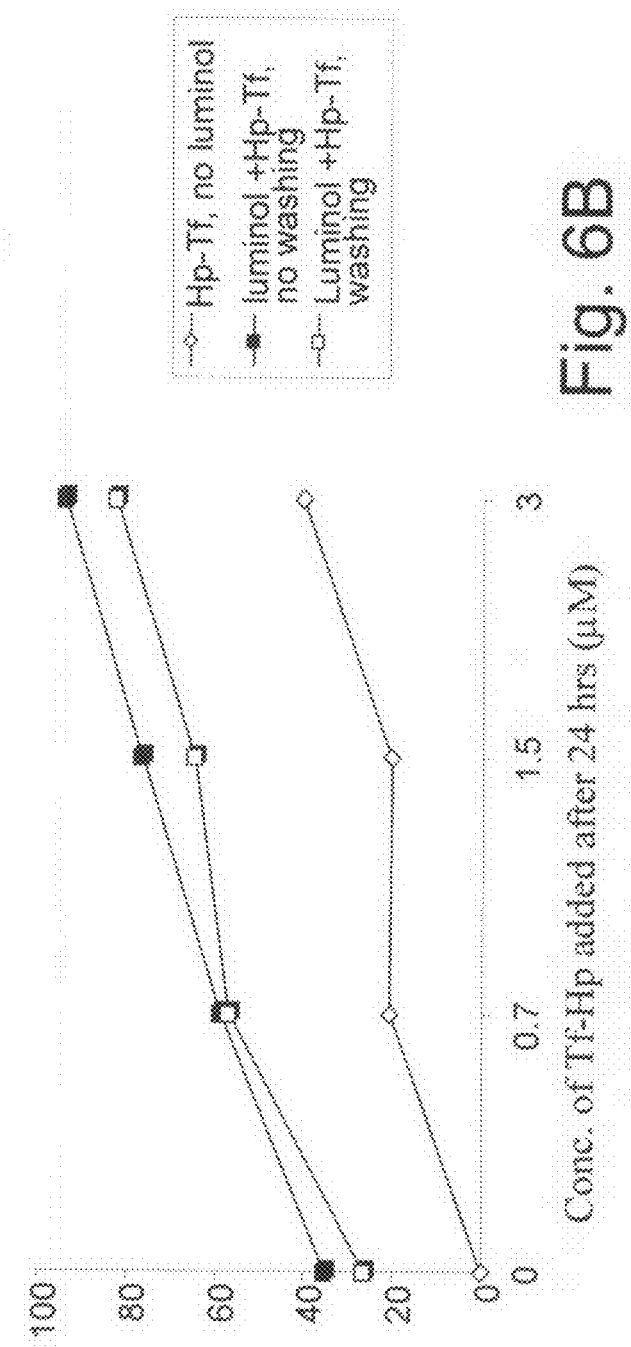
FIG. 6B shows the effect of pretreating FL cells by luminol on the cell growth inhibition by Tf-Hp. The cells were first cultured for 24 hrs in the presence of 10 µM luminol in the dark for 24 hr, washed or non-washed and then cultured for a further 24 hrs in the presence of Tf-Hp (0-3 µM) at 37° C.

Further evidence for the increased cytotoxicity of Tf-Hp over free Hp was obtained from fluorescence microscopy, which illustrated the presence and location of the Ps in FL cells after 45 and 60 minutes incubation with either Hp or Tf-Hp. At both time points, relatively faint (as no anti bleaching solution was used) Hp fluorescence was observed mainly constrained to the plasma membrane region. Significantly greater fluorescence was apparent in cells treated with Tf-Hp. After 45 minutes the conjugate localized in membrane patches (possibly demarcating endolysosomal compartments) and had infiltrated much of the cytoplasm by 60 minutes Further, the ability of an intracellular chemiluminescent light signal to induce PDT was tested. FIG. 4 illustrates the cytotoxicity induced in FL cells cultured in the dark with Hp or Tf-Hp either alone or together with 10 μM luminol. The cells were not exposed to ambient fluorescent light at any stage of the procedure. It was found that i) luminol alone induced about 15% cytotoxicity, (ii) Hp alone had little effect on cell viability, (iii) cytotoxicity reached a maximum of 30% in the presence of Hp and luminol and iv) luminol induced a significant (95%) PDT effect upon addition of Tf-Hp. FIG. 5 further demonstrates that the cytotoxic luminol-induced PDT effect is dependent on the concentration of both Tf-Hp and luminol with a combination of 10 μM luminol and 3 μM of conjugate producing maximum cytotoxicity. A reduction in Tf-Hp concentration had less effect on cytotoxicity than did lowering the level of luminol. It was checked whether the synchrony in exposure to luminol and Tf-Hp is a requirement for this cytotoxicity by incubating cells first with Tf-Hp, washing and then exposing them to luminol following various delay times. The time taken to wash the cells and return them to culture was approximately 15 minutes. While delaying the exposure to luminol by 30 minutes had no effect on the cytotoxicity (FIG. 6A), after 60 minutes of delay, the PDT effect was reduced by 50%. However by reversing the protocol, (FIG. 6B) it was found that pre-incubation with luminol for 24 hrs sensitized the cells to the delayed exposure to Tf-Hp and the PDT effect was dose dependent.

This invention addresses two problems of PDT technology. The first problem concerns the development of PDT systems to enhance the efficiency of Ps delivery to target cells. Most targeted PDT studies have used monoclonal antibodies as the address moiety. As the use of antibodies poses several practical limitations, an alternate approach may target a Tf-Ps conjugate to Tf receptors. The therapeutic potential of Tf-protein [Weaver M. et al.: J Neurooncol. 65 (2003) 3-13], and Tf-chemical [Singh M. et al.: Anticancer Res. 18 (1998) 1423-7] toxin conjugates have already been examined, but less is known about Tf-Ps conjugates particularly with regard to Hp which, although having been used successfully in free form in the clinic for over a decade [Dolmans D. E. et al.: Nature Reviews Cancer 3 (2003) 380-7], it has been little tested in targeted PDT [Hamblin M. R. et al.: J. Photochem. Photobiol. 26 (1994) 45-56]. The instant invention provides Tf-Hp conjugates that are at least 6-fold more effective in inducing cell death even at the $LD_{50}$ level (FIG. 2 and Table 1).

Aside from increasing target specificity and efficiency, PDT induced cell death is faster when Tf-Hp is used. For example during optimization of the LTC cytotoxicity assay, it was found by us that while almost 100% cytotoxicity was achieved after only 30 minutes exposure to Tf-Hp, about 2 hr were required for maximum activity (24%) of free Hp. Moreover, fluorescence microscopy of Hp and Tf-Hp-treated FL cells demonstrated that Tf-Hp is taken up more rapidly and that it reaches intracellular organelles, and this would provide for more effective disruption of intracellular membranes.

The second problem of PDT technology is addressed by the invention, concerning the source of the luminescent activating signal delivered to the Ps. An external radiation provides homogeneous excitation of Ps in the tissue culture or during subcutaneous injection, however the penetration of visible light into internal tissue is limited to a few millimeters, precluding the use of PDT for deeper tissue targets. Efforts to overcome this limitation have concentrated on new external light devices or improved catheters. The aim of the invention was to provide a molecular light-emitting mechanism within the Ps-loaded target cell. This strategy is non-invasive, does not expose normal tissue to irradiation and a molecular illuminator can be transported to target cells in vivo. We use the term Intracellular Activation of PDT (IAP) to describe such molecular systems.

Luminol is a chemiluminescent activator that undergoes a light emitting process catalyzed by metal ions and hydrogen peroxide. This process is employed in chemiluminescent detection techniques and in cell physiology studies, but the invention takes advantage of luminol as an energy source in the field of PDT of cancer cells. The emission spectrum of luminol comprises two major peaks, at 424 and 485 nm. It was observed by us that the first peak corresponded to a crest in the absorption spectrum of Tf-Hp (412 nm, FIG. 1), suggesting, together with the enhanced intracellular uptake of the Tf-Hp relative to Hp, that an IAP involving luminol is effective. Initially Hp or Tf-Hp was mixed with luminol and added to FL cell culture in the dark (FIG. 4). High concentrations of Tf-Hp alone induced low-level cytotoxicity in accordance with previous reports [Supino R. et al.: Chem. Biol. Interact. 57 (1986) 258-94; Luksiene Z. et al.: Medicina 39 (2003) 677-82], an effect that may be related to the ability of Hp to inhibit the activity of protein kinase C. Not only was there a significant PDT effect when both Tf-Hp and luminol were added to the cells, but the cytotoxic efficiency of Tf-Hp over Hp was even more enhanced than that seen with the external light source (FIG. 2). However the concentration of Tf-Hp required to reach $LD_{MAX}$ in the IAP system was 6.7 times higher than with external radiation (FIG. 4 and Table 1). In a previous study, Carpenter [Carpenter S. et al.: Proc. Natl. Acad. Sci. USA 91 (1994) 12273-7] described a bioluminescent IAP system for PDT that induced killing of virus-infected cells, involving the activation of hypericin following oxidation of luciferin by luciferase.

Additional experiments assessed whether or not the Ps and IAP systems need to be applied simultaneously in order to produce an effective PDT response (FIG. 6). Delaying addition of luminol to Tf-Hp-loaded cells by 45 minutes did not reduce cytotoxicity and as the cells were thoroughly washed before exposure to luminol these results reflect activation of intracellular Tf-Hp rather than material loosely bound to the membrane. Delaying exposure to luminol by a further 30 minutes decreased the PDT effect by half suggesting that the Tf-Hp residence time is a limiting factor in this system. When the components were added in the reverse order luminol-loaded cells remained very sensitive to PDT even when addition of Tf-Hp was delayed for 24 hrs.

As mentioned, Photodynamic Therapy (PDT) involves a two-stage process. In the first step, a light-absorbing photosensitizer (Ps) (for instance hematoporphyrin, Hp), is endocytosed. In the second step, the Ps is activated by light, transferring energy to a cytoplasmic acceptor molecule that activates molecular oxygen, yielding reactive oxygen species (ROS) that damage the cellular components, particularly membrane phospholipids. The outcome of this process leads to cytolysis. Efforts to expand the use of PDT in the clinic have been hindered by the lack of Ps target cell specificity and lack of tissue penetration of external light radiation. The invention provides bioconjugates comprising the carrier protein transferrin and Hp (Tf-Hp) that significantly improve the specificity and efficiency of PDT for erythroleukemic cells by a factor of almost 20-fold at the $LD_{50}$ level. Fluorescence microscopy showed that the conjugates are endocytosed and accumulate in intracellular vesicles whereas free Hp was mostly membrane bound. In addition, it was shown by the inventors that the use of external radiation for Ps activation can be bypassed by incubating the cells with luminol either prior to or together with Tf-Hp. Luminol is activated intracellularly to yield chemiluminescent radiation that stimulated PDT-induced cytotoxicity in 95% of cells. These strategies provide safer and more effective applications of PDT.

The present invention provides a new approach to overcome the limitations of PDT applications. The efficacy of the targeted LTC strategy using the Tf-Hp system is first established, and then in vitro applicability of luminol is demonstrated, wherein luminol can be used as a powerful molecular inducer of intracellular CL for the destruction of leukemic cells, obviating the use of external light sources in PDT.

In conclusion, the invention provides Tf-Hp conjugates as a viable vehicle for PDT induced cytotoxicity. Enhanced targeting of the Ps with carrier proteins that are efficiently endocytosed increase therapeutic efficacy of PDT by reducing dosage and overcoming toxicity to normal tissue inevitably produced with free Ps. The invention thus provides means for destroying cells associated with proliferative diseases, for example cancer.

The invention will be further described and illustrated in the following examples.

EXAMPLES

General Procedures

Hp, rabbit anti-human transferrin, goat anti-bovine serum albumin, transferrin, N-hydroxysuccinimide (NHS) and luminol were purchased from Sigma-Aldrich Chemical Co. N,N-dicyclohexyl carbodiimide (DCC) and tetrahydrofuran (THF) were from Carlo Erba. Horse serum (HS), Fetal Calf Serum (FCS), L-glutamine and combined antibiotics were purchased from Biological Industries Ltd. (Bet Haemek, Israel). HPLC solvents were from Merck.

Cells

U-76 is a murine hybridoma that secretes IgG1 antibody against dinitrophenol (DNP) and was a kind gift of Prof. Eshhar (Weizmann Institute of Science, Rehovot, Israel). These cells as well as Friend's Leukemia (FL) cells were grown in DMEM containing 15% HS, 2 mM L-glutamine and combined antibiotics. Human K-562 cells were grown in RPMI/15% HS/glutamine/antibiotics. All cells were maintained at 37° C. in a humidified incubator containing 6% $CO_2$.

Preparation of Hp Containing LTCs 0.11 mmole hematoporphyrin hydrochloride was dissolved in 10 ml chloroform and activated by addition of 0.173 mmole of NHS and 0.11 mmole DCC. The mixture was stirred at room temperature for 2.5 hrs. Following evaporation with a stream of air, the residue was dissolved in 2 ml of THF and the activated Hp was slowly added to a solution of 15 mg transferrin dissolved in 10 ml of 0.1M $NaHCO_3$ cooled on ice. The solution was allowed to warm to room temperature, adjusted to pH 7.5 and stirred vigorously overnight. Tubes containing Hp were protected from light exposure. The conjugate solution was centrifuged (7200×g, 30 mins, 4° C.) and the supernatant was analyzed spectroscopically for the content of protein ($\lambda$=280 nm) and Hp ($\lambda$=400 nm). After dialysis, a small portion of the crude reaction product was chromatographed over Sephadex G-50 equilibrated with 5 mM $NaHCO_3$ (pH 8.0) or 10 mM PBS (pH 7.2). Fractions containing materials with absorption peaks at 280 and 400 nm were collected and stored at 4° C. HPLC: Tf, Hp and Tf-Hp were chromatographed over a C-18 column (3.9 mm×300 mm Bondclone, particle diameter 10 μm, Phenomenex) using a HPLC JASCO-1580 with a JASCO 1575 UV/VIS detector. The solvent system was composed of acetonitrile-water with 1% trifluoroacetic acid and compounds were eluted with a linear gradient (20-100% acetonitrile).

Absorbance spectrum: The absorbance spectra of PBS solutions of Hp (0.02 mg/ml), Tf (1.4 mg/ml) and Hp-Tf (1.4 mg/ml) were recorded with a CHEMUSB2-UV-VIS spectrophotometer having optical resolution of 1 nm, grating of 600 lines per mm equipped with CCD array detector. The samples were scanned in the absorbance region of 250-500 nm.

Biological Activity: This was assessed by the ability of anti-transferrin or anti-BSA antibodies to inhibit PDT-induced cytotoxicity and was tested using FL cells exposed to Tf-Hp either alone or together with varying concentrations of each antibody.

LTC Cytotoxicity Assay

Late log-phase cells were washed with DMEM prewarmed to 37° C. and cultured at $0.5$-$1\times10^5$ cells/ml either alone or with increasing concentrations of Tf-Hp LTC for 2 hrs at 37° C. in 6% $CO_2$. Cells were then washed with DMEM, exposed to ambient fluorescent light (fluence rate=0.5 mW/cm$^2$) for 12-16 hours and then re-cultured in full medium for 24 hrs. Cell viability was determined by trypan blue exclusion. Experiments were repeated at least three times. The optimal exposure times of cells to the Ps and fluorescent radiation were determined in preliminary time-course experiments.

Fluorescence Microscopy of Hp and Tf-Hp Endocytosis

FL cells were grown on glass slides in tissue culture dishes together with Hp or Tf-Hp and the incorporated fluorescence was followed at various time intervals with an AX70 Olympus microscope equipped with a high-pressure mercury lamp for excitation and a set of filters for blue violet excitation (band path 420-480 nm), dichroic mirror (455 nm) and a cut-on red emission barrier filter (580 nm). Fluorescence was analyzed with an X60 objective, without addition of any anti bleaching solution, and recorded by a CCD camera.

Intracellular PDT Activation by Luminol

FL cells were washed and cultured for 20 hrs with different concentrations of Hp or Tf-Hp (0.07, 0.15 or 0.3 μM) together with luminol (0-10 μM). Manipulations of cells and components were performed with the room lights switched off. Culture plates were wrapped in aluminum foil during the culture period. Subsequently, experiments aimed to test whether a PDT effect could be obtained by staggering the exposure of the cells to either luminol or Tf-Hp conjugate. FL cells were cultured for 2 hrs in the dark at 37° C. with Tf-Hp (3 µM), washed and re-suspended in medium at the standard culture concentration. This procedure took approximately 15 minutes. Then, the cells were kept at 37° C. for an additional 0, 30, 60 or 90 minutes, luminol (10 µM) was added and the cultures incubated in the dark for a further 16 hrs. Alternatively, cells were first cultured for 24 hrs in the dark in the presence of 10 µM luminol, washed or not-washed and then cultured further for 24 hrs in the presence of Tf-Hp (0-3 µM) at 37° C. During washing procedures and cell handling, special care was taken to maintain the cells in a dark environment.

While this invention has been described in terms of some specific examples, many modifications and variations are possible. It is therefore understood that within the scope of the appended claims, the invention may be realized otherwise than as specifically described.

The invention claimed is:

1. A method for selectively destroying target cells, the method comprising:
   (i) contacting the target cells with a ligand-toxin conjugate (LTC) which comprises a photosensitizer (Ps) and a transport ligand linked to the photosensitizer; and
   (ii) exposing the target cells to a chemiluminescent agent which reacts with an oxygen species present in situ and produces chemiluminescent light, thereby causing direct damage to the cellular components of said target cells.

2. A method according to claim 1, wherein said ligand in said ligand-toxin conjugate comprises a peptide.

3. A method according to claim 2, wherein said peptide is recognized by a receptor on the surface of the target cells.

4. A method according to claim 2, wherein said peptide is transferrin.

5. A method according to claim 1, wherein said photosensitizer comprises hematoporphyrin.

6. A method according to claim 1, wherein said ligand-toxin conjugate comprises transferrin and hematoporphyrin being linked to the transferrin.

7. A method according to claim 1, wherein said chemiluminescent agent comprises a luminol or a luminol derivative.

8. A method according to claim 6, wherein said chemiluminescent agent comprises a luminol or a luminol derivative.

9. A method according to claim 1, wherein said chemiluminescent agent is selected from the group consisting of luminol, isoluminol and lucigenin.

10. A method according to claim 1, wherein said chemiluminescent agent is coupled to said ligand-toxin conjugate.

11. A method according to claim 1, wherein said ligand-toxin conjugate is capable of accumulating in intracellular vesicles.

12. A method according to claim 1, wherein said ligand-toxin conjugate and said chemiluminescent agent act in synergy in destroying the target cells.

13. A method of treating a disorder associated with undesired activity of a cell population in a subject in need thereof, the method comprising administering to the subject a chemiluminescent agent which reacts with an oxygen species present in situ and produces chemiluminescent light, and a ligand-toxin conjugate which comprises a photosensitizer and a transport ligand linked to the photosensitizer, thereby destroying the cells in said cell population.

14. A method according to claim 13, wherein said undesired activity is an enhanced proliferation.

15. A method according to claim 13, wherein said ligand in said ligand-toxin conjugate comprises a peptide.

16. A method according to claim 15, wherein said peptide is recognized by a receptor on the surface of the target cells.

17. A method according to claim 15, wherein said peptide is transferrin.

18. A method according to claim 13, wherein said photosensitizer comprises hematoporphyrin.

19. A method according to claim 13, wherein said ligand-toxin conjugate comprises transferrin and hematoporphyrin being linked to the transferrin.

20. A method according to claim 13, wherein said chemiluminescent agent comprises a luminol or a luminol derivative.

21. A method according to claim 13, wherein said chemiluminescent agent is selected from the group consisting of luminol, isoluminol and lucigenin.

22. A method according to claim 13, wherein said chemiluminescent agent is coupled to said ligand-toxin conjugate.

23. A method according to claim 13, wherein said ligand-toxin conjugate is selected capable of accumulating in intracellular vesicles.

24. A method according to claim 13, wherein said ligand-toxin conjugate and said chemiluminescent agent act in synergy in destroying the cells in said cell population.

25. A method according to claim 13, wherein said disorder is associated with cancer or hyperplasia.

26. A pharmaceutical composition comprising a ligand-toxin conjugate which comprises a photosensitizer and a transport ligand linked to the photosensitizer, said ligand-toxin conjugate having a chemiluminescent agent covalently coupled thereto.

* * * * *